United States Patent
Doss

(10) Patent No.: US 8,795,221 B2
(45) Date of Patent: Aug. 5, 2014

(54) BYPASS DEVICE FOR INFLUENCING BLOOD PRESSURE

(75) Inventor: Mirko Doss, Frankfurt am Main (DE)

(73) Assignee: E.S. Bio-Tech Limited, Limassol (CY)

( * ) Notice: Subject to any disclaimer, the term of this patent is extended or adjusted under 35 U.S.C. 154(b) by 77 days.

(21) Appl. No.: 12/927,103

(22) Filed: Nov. 5, 2010

(65) Prior Publication Data

US 2011/0130700 A1 Jun. 2, 2011

(30) Foreign Application Priority Data

Nov. 7, 2009 (DE) .......................... 10 2009 052 349

(51) Int. Cl.
| | |
|---|---|
| *A61M 5/00* | (2006.01) |
| *A61M 1/10* | (2006.01) |
| *A61F 2/06* | (2013.01) |
| *A61F 2/07* | (2013.01) |
| *A61F 2/30* | (2006.01) |

(52) U.S. Cl.
CPC ................ *A61M 1/1037* (2013.01); *A61F 2/06* (2013.01); *A61F 2/07* (2013.01); *A61M 1/10* (2013.01); *A61F 2002/068* (2013.01); *A61F 2002/30069* (2013.01); *A61F 2002/30074* (2013.01); *A61F 2002/30548* (2013.01); *A61F 2210/0057* (2013.01); *A61F 2250/0013* (2013.01)
USPC .................. 604/9; 604/8; 623/1.1; 623/1.15; 623/1.28; 623/1.3; 623/1.49; 623/23.64; 623/23.67; 606/153; 606/158

(58) Field of Classification Search
CPC ......... A61F 2/06; A61F 2/07; A61F 2002/06; A61F 2002/068; A61F 2002/07; A61F 2002/30069; A61F 2002/3007; A61F 2002/30074; A61F 2002/30548; A61F 2210/0057; A61F 2250/0013; A61M 2001/122; A61M 2001/125; A61M 1/1037; A61M 1/1067; A61M 1/1068; A61M 1/1086; A61M 1/107
USPC ................ 604/8, 9; 623/1.1, 1.15, 1.17, 1.21, 623/1.28, 1.29, 1.3, 1.49, 23.64, 23.67; 606/153, 158
See application file for complete search history.

(56) References Cited

U.S. PATENT DOCUMENTS 4,938,766 A * 7/1990 Jarvik .......................... 623/3.17
5,007,927 A * 4/1991 Badylak et al. .............. 623/3.12

(Continued)

FOREIGN PATENT DOCUMENTS

| DE | 10 2004 018 255 A1 | 11/2005 |
|---|---|---|
| DE | 10 2006 020 687 A1 | 2/2007 |

(Continued)

OTHER PUBLICATIONS

Daniel Burkhoff, Israel Mirsky, Hiroyuki Suga. "Assessment of systolic and diastolic ventricular properties via pressure—volume analysis: a guide for clinical, translational, and basic researchers." American Journal of Physiology—Heart and Circulatory Physiology. Aug. 1, 2005. vol. 289, No. H501-H512. DOI:10.1152/ajpheart. 00138.2005.*

*Primary Examiner* — Adam Marcetich

(74) *Attorney, Agent, or Firm* — Pauley Petersen & Erickson

(57) ABSTRACT

A bypass device for influencing blood pressure, including an implant with a volumetric chamber, having a connector or connecting means for connecting the volumetric chamber to a natural cardiovascular system, and having an adaptor or adaptation means, by which a change in volume of a volume of the volumetric chamber is enabled or effected upon a pressure change in the cardiovascular system or in the volumetric chamber. According to this invention, a change in volume in a lower pressure range between 50 mmHg and a pressure threshold value amounting to at least 100 mmHg amounts to at most 10 cm$^3$, and in an upper pressure range between the pressure threshold value and 150 mmHg amounts to at least 10 cm$^3$. With the device according to this invention, high blood pressure can be reduced in a carefully directed way.

9 Claims, 4 Drawing Sheets

(56) References Cited

U.S. PATENT DOCUMENTS

| | | | |
|---|---|---|---|
| 5,267,940 A * | 12/1993 | Moulder | 600/16 |
| 6,450,942 B1 | 9/2002 | Lapanashvili et al. | |
| 2002/0103413 A1* | 8/2002 | Bugge et al. | 600/16 |
| 2003/0088151 A1* | 5/2003 | Kung et al. | 600/37 |
| 2004/0088042 A1* | 5/2004 | Kim et al. | 623/1.16 |
| 2004/0098096 A1 | 5/2004 | Eton | |
| 2004/0106971 A1* | 6/2004 | Schwartz et al. | 623/1.1 |
| 2004/0133260 A1* | 7/2004 | Schwartz et al. | 623/1.1 |
| 2004/0143319 A1 | 7/2004 | Schwartz et al. | |
| 2006/0217588 A1 | 9/2006 | Gross et al. | |
| 2006/0253193 A1* | 11/2006 | Lichtenstein et al. | 623/3.1 |
| 2007/0162106 A1 | 7/2007 | Evans et al. | |
| 2007/0287879 A1 | 12/2007 | Gelbart et al. | |
| 2007/0293932 A1* | 12/2007 | Zilla et al. | 623/1.11 |
| 2008/0033527 A1 | 2/2008 | Nunez et al. | |
| 2008/0071133 A1* | 3/2008 | Dubi | 600/16 |
| 2008/0194905 A1 | 8/2008 | Walsh | |
| 2008/0234537 A1 | 9/2008 | Gross | |
| 2009/0112305 A1 | 4/2009 | Goldmann et al. | |
| 2009/0240277 A1 | 9/2009 | Connors et al. | |

FOREIGN PATENT DOCUMENTS

| | | |
|---|---|---|
| DE | 10 2005 058 409 A1 | 6/2007 |
| WO | WO 89/01765 A1 | 3/1989 |
| WO | WO 00/64387 | 11/2000 |
| WO | WO 2005/084730 A1 | 9/2005 |

* cited by examiner

BYPASS DEVICE FOR INFLUENCING BLOOD PRESSURE

BACKGROUND OF THE INVENTION

1. Field of the Invention

This invention relates to a bypass device for influencing blood pressure, including an implant with a volumetric chamber, having connecting means for connecting the volumetric chamber to a natural cardiovascular system, and having an adaptation by which a change in volume of a volume of the volumetric chamber is enabled or effected upon a pressure change in the cardiovascular system or in the volumetric chamber.

2. Discussion of Related Art

German Patent Disclosure DE 10 2004 018 255 A1 discloses an implant in the form of a vascular prosthesis, which is embodied essentially as a tube with an elastic inner wall. A nonwoven structure limits the stretchability of the elastic inner wall, so that a flexural strength behavior is attained that is essentially equivalent to the extensibility of natural arteries at both systolic and diastolic pressure. Thus the vascular prosthesis can restore or reinforce the so-called Windkessel effect of the natural arteries and in particular of the aorta. The term "Windkessel function" is understood to mean the retention of some of the blood volume ejected by the heart during systole in the elastic central arteries, and its continuous output during diastole. The Windkessel function makes the arterial blood flow in the peripheral circulatory system more uniform. A reduced or impeded wk function of natural arteries relates to fundamentally more work for the heart, and over the long term, the risk of heart damage rises. With the elastic inner wall of the vascular prosthesis taught by German Patent Disclosure DE 10 2004 018 255 A1, a greater quantity of blood is briefly stored as a result of stretching of the inner wall during systole, the ejection phase of the heart. During diastole, relaxation of the heart muscle, the blood briefly stored in the vascular prosthesis is forced out of the vascular prosthesis again because of the elasticity of the inner wall.

From German Patent Disclosure DE 10 2005 058 409 A1 as well, an implant is known as a replacement for a portion of the aorta or an artery, the volume of the implant being elastically deformable by a spring incorporated into the vessel wall. This implant, too, reinforces the Windkessel effect.

U.S. Pat. No. 6,450,942 B1 discloses an implant for regaining or increasing the resilience of the natural arterial system in order to improve the arterial blood flow. This is intended to reduce the load on the heart muscle, because the heart muscle can perform its work more effectively.

Although by the known devices from the prior art the natural Windkessel effect can be simulated or reinforced, and thus a blood pressure reducing effect is attained, these devices can be employed only to a very limited extent for the treatment of high blood pressure. It appears that continued intake of medications by the patient continues to be necessary. Taking medications can be accompanied by sometimes major or harmful side effects, so that a middle ground is found between the requisite blood pressure regulation and the influence on the welfare of the patient. Also, the success of this form of therapy is largely dependent on the compliance of the patient in taking medications.

SUMMARY OF THE INVENTION

It is one object of this invention to provide a device for influencing blood pressure by which high blood pressure, in particular, can be treated effectively and, as much as possible, without the patient having to take medications.

This object of this invention is attained with the combination of characteristics of exemplary embodiments described in this specification and in the claims.

The device for influencing blood pressure according to this invention, in particular a bypass device, is distinguished because the change in volume in a lower pressure range between 50 mmHg and a pressure threshold value amounting to at least 100 mmHg amounts to at most 10 cm$^3$, and in an upper pressure range between the pressure threshold value and 150 mmHg amounts to at least 10 cm$^3$. The change in volume in the lower pressure range should be understood to mean that at a pressure rise from 50 mmHg to the pressure threshold value of 100 mmHg, the volume of the volumetric chamber increases by 10 cm$^3$ at most. Correspondingly, the volume of the volumetric chamber in the upper pressure range, upon a pressure rise from 100 mmHg to 150 mmHg, should increase by at least 10 cm$^3$.

The subject matter can preferably be made still more specific based on the ratio of the differential change in volume to the differential pressure change, which corresponds to the slope of a curve in a V-p graph. Thus the differential change in volume per differential pressure change, for pressure values in a lower pressure range between 50 mmHg and a pressure threshold value amounting to at least 100 mmHg, can amount to at most 0.2 cm$^3$/mmHg, and in an upper pressure range between the pressure threshold value and 150 mmHg, can amount to at least 0.2 cm$^3$/mmHg.

In addition, a bypass device for influencing the blood pressure is disclosed, including an implant with a volumetric chamber, having a connection or connecting means for connecting the volumetric chamber to a natural cardiovascular system, and having an adaptor or adaptation means, by which a change in volume of a volume of the volumetric chamber is enabled or effected upon a pressure change in the cardiovascular system or in the volumetric chamber, in which the differential change in volume per differential pressure change for pressure values in a lower pressure range between 50 mmHg and a pressure threshold value amounting to at least 100 mmHg amounts to at most 0.2 cm$^3$/mmHg and in an upper pressure range between the pressure threshold value and 150 mmHg amounts to least 0.2 cm$^3$/mmHg.

In a preferred exemplary embodiment, the pressure threshold value amounts to at least 120 mmHg. Equally good values in the treatment of high blood pressure can be attained if the pressure threshold value is above 130 mmHg or even 140 mmHg.

For arterial pressure measurement, two values are typically ascertained. The upper or first value is called the systolic arterial pressure. It characterizes the pressure in the heart at the moment when the heart muscle maximally retracts. As soon as the heart muscle relaxes, the arterial pressure drops to the second or lower pressure, the diastolic arterial pressure. Arterial high blood pressure exists if upon repeated measurement, a value of 140 mmHg for the first value and 90 mmHg for the second value are attained.

With the bypass device with the implant according to this invention, which has a volumetric chamber whose volume varies only very little in the pressure range below the pressure threshold value (lower pressure range) but can vary quite sharply in the pressure range above the pressure threshold value (upper pressure range), arterial high blood pressure can be treated in a carefully directed way.

The bypass device according to this invention, which is preferably implanted parallel to a portion of a natural blood vessel, increases the volume of the natural cardiovascular system artificially, and thus forms a volumetric buffer of variable size, which particularly at high pressures in the system can briefly absorb a certain quantity of blood and output it again when the system pressure lets up.

In the lower pressure range only slight changes in volume of the volumetric chamber occur and any possible influence of the implant on the Windkessel effect in the lower pressure range is slight. In the upper pressure range, conversely, major changes in volume are allowed, which can go beyond the changes in volume which would be established by the natural Windkessel effect under those pressure conditions. In the upper pressure range, because of the comparatively large changes in volume, incident pressures can be reduced effectively and in a carefully directed way. The pressure threshold value, as already noted above, can be below the systolic arterial pressure of 140 mmHg beyond which, after repeated measurement, arterial hypertension is presumed.

The change in volume in the lower pressure range between 50 mmHg and the pressure threshold value can be limited to at most 5 cm$^3$. An even stricter maximum value is 3 cm$^3$, so that in the lower pressure range, virtually no change in volume in the volumetric chamber of the implant occurs.

In the upper pressure range, conversely, between the pressure threshold value and 150 mmHg, the change in volume can amount to markedly more than 10 cm$^3$. For instance, at least 15 cm$^3$ can be set as the lower limit for the change in volume in the upper pressure range. Preferably, the lower limit value is 20 cm$^3$ or even 25 cm$^3$.

For pressure values in the lower pressure range between 50 mmHg and the pressure threshold value, the ratio of the differential change in volume to the differential pressure change can amount to at most 0.1 cm$^3$/mmHg or even at most 0.06 cm$^3$/mmHg. In the upper pressure range, between the pressure threshold value and 150 mmHg, the differential change in volume per differential pressure change can amount to at least 0.3 cm$^3$/mmHg, at least 0.4 cm$^3$/mmHg, or even at least 0.5 cm$^3$/mmHg.

The adaptation means, by which a change in volume in the volume of the volumetric chamber is enabled or effected upon a pressure change in the cardiovascular system or in the volumetric chamber, can have an energy storage or storing means, which upon a pressure increase absorbs energy and upon a pressure drop outputs energy. For example, if a pressure of 140 mmHg is reached at systole, the adaptation means absorb energy, thereby avoiding an otherwise greater pressure increase. In diastole, a pressure drop can be observed and the energy storing means now outputs its energy and forces blood out of the volumetric chamber, and as a result the pressure drop is less pronounced.

The energy storing means can have an elastic material, which preferably at least partly defines the volumetric chamber. Upon a pressure increase, this elastic material expands, and then upon a pressure drop it relaxes again in the direction of its original shape. The energy storing means can alternatively or in addition include spring devices, which impose a defined geometric shape on the volumetric chamber that changes upon a pressure change. For instance, the implant could have the form of a cylinder, and the spring devices compress the cylindrical cross section to an elliptical cross section, with the consequence that the volume is reduced accordingly. Upon a pressure increase in the implant, a virtually cylindrical cross section is again reached, counter to the force of the spring devices, and as a result the volume of the implant increases accordingly. Upon a pressure drop, in turn, the spring devices force the implant back into the shape with the elliptical cross section. The volume is reduced further.

The adaptation means may include mechanical and/or electrical components. It is also conceivable for the adaptation means to have magnets, by which a change in volume of the volumetric chamber can be influenced in a carefully directed way.

In a preferred exemplary embodiment, the pressure threshold value is adjustable. Preferably, the pressure threshold value can be adjusted from outside. For instance, the pressure threshold value could be adjusted from outside by way of a suitable triggering of the implant, such that certain blood pressures of the patient are not exceeded. Thus the pressure threshold value can be set individually for each patient. It is also conceivable for the pressure threshold value to be adjusted as a function of the coronary circulation. Compared to a very moderate load, for instance, a different pressure threshold value can be set for expected heavy loads.

The term "adjustable from outside" thus means that the pressure threshold value can be varied even if the implant has already been implanted. However, it is also possible for the pressure threshold value to be adjusted directly in the implant before implantation, by way of suitable adjustments. Thus an implant could be produced which can then be adjusted individually, prior to implantation, for different patients and different requirements.

Preferably, the implant has a controller, with a sensor with which a pressure in the cardiovascular system or in the volumetric chamber can be detected. Preferably, the controller can output a signal when the pressure threshold value, or a value that correlates with the pressure threshold value, is reached, and this signal can be output to the adaptation means. For instance, if the pressure detected by the sensor is below the pressure threshold value, then the adaptation means exhibit a different behavior with regard to the change in volume than in the case when the detected pressure is above the pressure threshold value.

Preferably, an outer guard is provided to protect against ingrowth into and/or an ingrowth of natural tissue on the volumetric chamber. As a result, it can be ensured that the volumetric chamber as well as the adaptation means are protected from natural tissue, or are not impaired in their functions by it.

If the pressure threshold value is adjustable from the outside, then suitable means are required for this arrangement. These means may include a receiver, which receives signals in contactless fashion from a transmitter that transmits externally. Also, the device can include a transmitter for enabling measured values for blood pressure, pulse rate, etc., to be read out. The exchange or transmission or reception can be done with the aid of electromagnetic waves, such as by means of radio frequency identification (RFID).

To influence the venous blood pressure, in addition to influencing the arterial blood pressure, a reservoir may be provided, which has a capacity of 100 ml to 1000 ml, and preferably 500 ml to 750 ml. The reservoir can be helical and/or spiral. In the preferred exemplary embodiment, the blood volume that the reservoir can hold can be predeterminable and calibratable, so that a set-point quantity of the venous blood volume can be set individually for each patient. This adjustment of the blood volume that can be held can be regulated from outside and as much as possible at the direction of a physician.

BRIEF DESCRIPTION OF THE DRAWINGS

This invention is described in further detail in view of exemplary embodiments shown in the drawings, wherein.

DETAILED DESCRIPTION OF THE INVENTION

Figure 1:
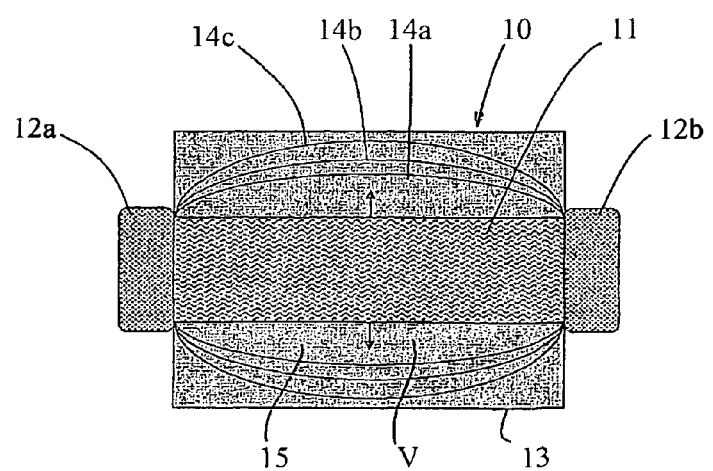
FIG. 1 shows a first exemplary embodiment for an implant according to this invention.

FIG. 1 shows a first exemplary embodiment for an implant according to this invention, which is identified overall by reference numeral 10. The implant 10 includes a biocompatible elastic tube 11, on the ends of which two rings 12a, 12b are secured. The rings 12a, 12b serve as stitching rings, to enable securing the implant in or on a cardiovascular system. The implant 10 furthermore has a biocompatible outer sheath 13, which is intended to prevent natural tissue from impairing the function of the elastic tube or hose 11.

Because of the elasticity of the tube 11, the tube 11 expands when the implant is subjected to a pressure. The lines 14a, 14b and 14c are intended to represent different deformation states of the tube 11, when a pressure prevails in the tube that presses the tube wall outward. The highest pressure exists in the deformation state 14c, while in the deformation state 14a the least pressure exists. The pressure in the deformation state 14b is between the pressures of the deformation states 14a, 14c.

As a result of the deformed tube 11, a volume V of a volumetric chamber 15, which is defined by the tube wall of the tube 11, also changes. In the deformation state 14c, the result is thus the greatest volume $V_c$ of the volumetric chamber 15 of the implant 10.

Figure 2:
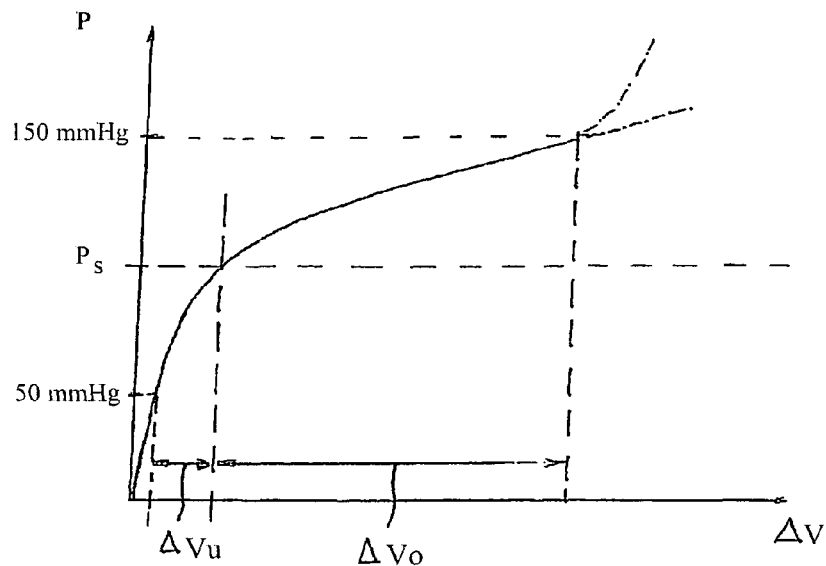
FIG. 2 shows a course of blood pressure plotted over a change in volume.

FIG. 2 shows the relationship between a blood pressure P in the volumetric chamber 15 and change in volume ΔV of the volume of the volumetric chamber 15. A lower pressure range and an upper pressure range are defined by a pressure threshold value $P_S$. The lower pressure range as shown in FIG. 2 extends from 50 mmHg to the pressure threshold value $P_S$, while the upper pressure range extends from the pressure threshold value $P_S$ to 150 mmHg. It can be seen from FIG. 2 that in the lower pressure range from 50 mmHg to the pressure threshold value $P_S$, only a slight change in volume $\Delta V_U$ results. In the upper pressure range, conversely, the change in volume $\Delta V_O$ is substantially greater than the change in volume $\Delta V_U$ in the lower pressure range.

In the exemplary embodiment of FIG. 2, the pressure threshold value $P_S$ is approximately 100 mmHg. According to the invention, the pressure threshold value $P_S$ can also assume different values, such as 110, 120, 130, or 140 mmHg. Because up to the pressure threshold value $P_S$ the change in volume is very slight, the influence of the implant 10 on the blood pressure of the patient is also slight. Only from the pressure threshold value $P_S$ onward does a markedly greater change in volume $\Delta V_O$ occur, so that then the implant has a significant influence on the blood pressure of the patient. Thus blood pressures above the pressure threshold value $P_S$, and in particular high blood pressure above 140 mmHg, can be influenced in a carefully directed way, without the implant 10 having substantial influence on the blood pressure at low blood pressures, such as below the pressure threshold value $P_S$.

Figure 3:
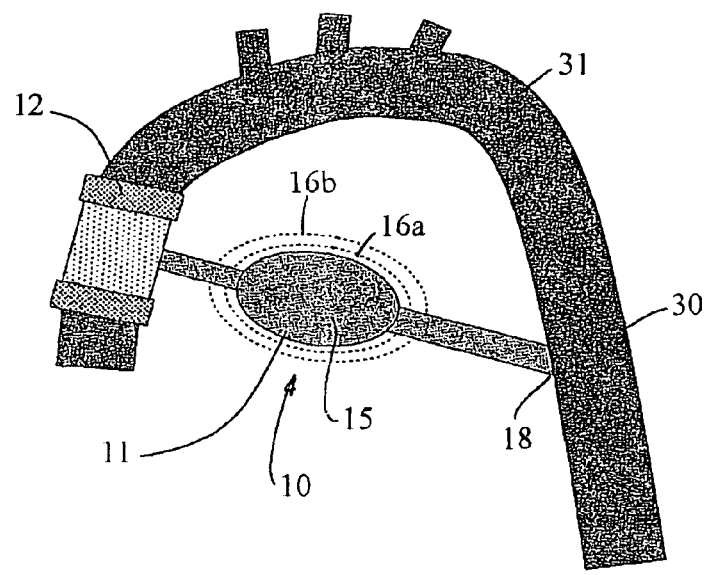
FIG. 3 shows a second exemplary embodiment of the implant according to this invention and an aortic arch.
Figure 4:
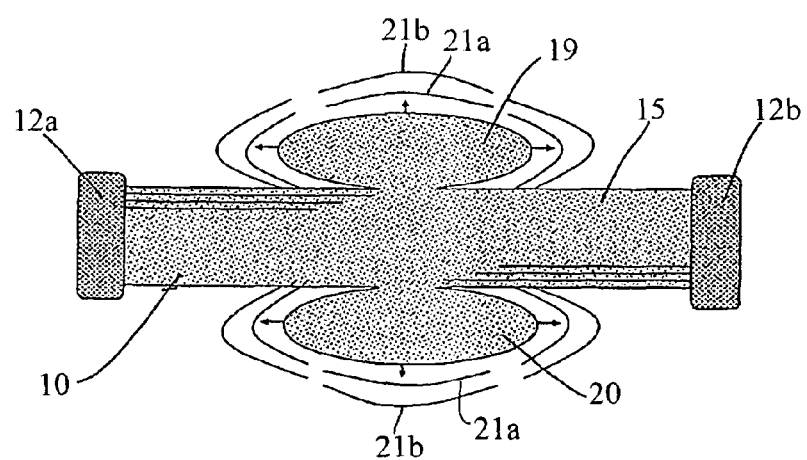
FIG. 4 shows a third exemplary embodiment of the implant according to this invention.

In FIGS. 3 through 5, further exemplary embodiments of the implant of the invention are shown and elements or characteristics that are similar or identical to the elements or characteristics of FIG. 1 are identified by the same reference numerals.

FIG. 3 likewise shows an implant 10, which is connected to an aorta 30 in such a way that the implant 10 is connected parallel to an upper portion 31 of the aorta. The dashed lines 16a, 16b in FIG. 3 indicate that the volume of the volumetric chamber 15 of the implant 10 is likewise variable. The implant 10 of FIG. 3 has a stitching element 17, which replaces a portion of the aorta 30. On a different end 18 of the implant 10, a ring not shown here is provided, in order to connect the end 18 of the implant to the aorta 30.

FIG. 4 shows an exemplary embodiment for the implant 10, again equipped with stitching rings 12a, 12b. Here, the implant 10 has expansible hollow chambers 19, 20, which have a suitable elasticity for influencing the blood pressure in the manner according to the invention. Once again, lines 21a, 21b serve the purpose of illustrating the fact that when the implant 10 is subjected to appropriate pressure, the hollow chambers 19, 20 expand and thus lead to a change in volume of the volumetric chamber 15 of the implant.

Figure 5A:
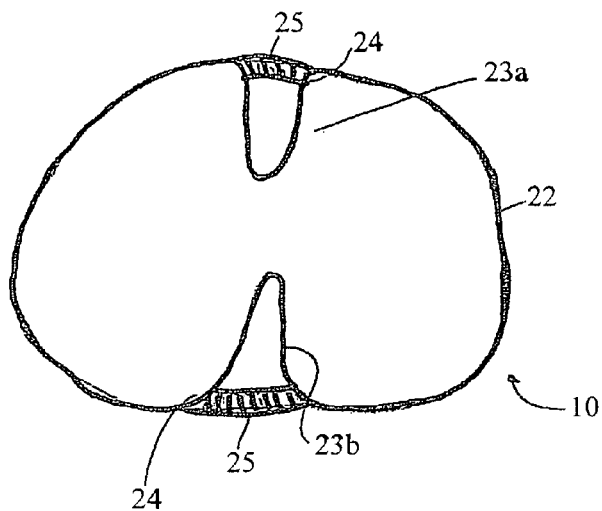
FIG. 5 shows further exemplary embodiments of the implant according to this invention.
Figure 5B:
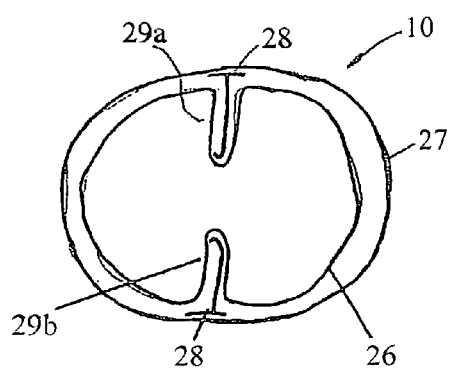
Figure 5C:
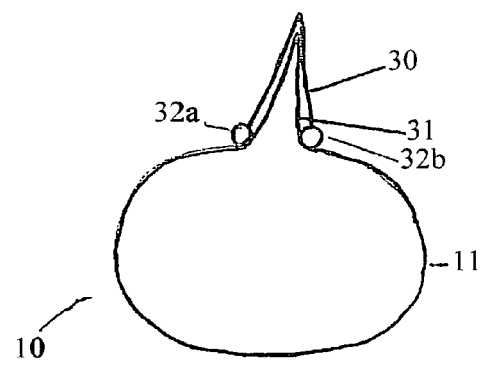

FIG. 5 (FIGS. 5a, 5b, 5c) now shows further exemplary embodiments for the implant 10 of the invention. Here, instead of longitudinal sections, schematic cross sections of the implant 10 are shown. In the exemplary embodiment of FIG. 5a, the implant 10 has a substantially circular hose cross section 22, which however has two inward-oriented indentations 23a, 23b. On the outer end 24 of each of the indentations 23a, 23b, there is a spring element 25, which is pulled apart when the implant is subjected to pressure. The elasticity of the spring element or means 25 in cooperation with the geometry of the hose cross section 22 is adjusted such that only beyond a certain pressure do the indentations disappear entirely and lead to an expansion of the cylindrical cross section 22, so that the volume of the implant 10 increases markedly.

The exemplary embodiment of FIG. 5b has an inner sheath 26 and an outer sheath 27. Between the inner sheath 26 and the outer sheath 27, there are two radially inward-oriented spring elements 28, which cause two radially inwardly located indentations or creases 29a, 29b to be created.

The exemplary embodiment of FIG. 5c has a clamp 30, put on from an outside, by which a deformable hose 11 of the implant 10 is compressed over a portion of the circumference of the hose 11. As a result, a crease 31 in the hose is created in the vicinity of or near the clamp 30. Upon a pressure increase in the hose 11, the ends 32a, 32b of the clamp are forced apart, which leads to an increased cross section of the hose 11 and thus to a greater volume of the implant 10.

The spring elements 25, 28 and 30 in cooperation with the indentations 23a, 23b, 29a, 29b as well as creases 31 can be designed so that a significant change in volume of the implant 10 does not occur until after the pressure threshold value is reached. Then, as soon as the pressure threshold value is reached, there is a completely new relationship between the pressure change and the change in volume.

Figure 6:
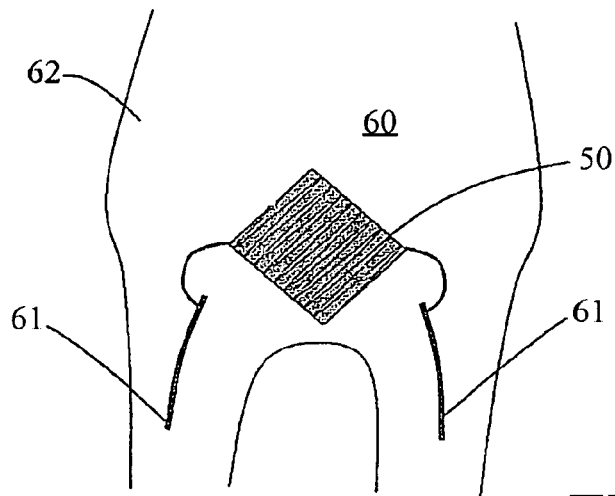
FIG. 6 shows a first exemplary embodiment for a venous reservoir.

FIG. 6 shows an exemplary embodiment for a venous reservoir 50 according to this invention. The venous reservoir 16 can hold a certain quantity of blood. The vt 50 can, as shown in FIG. 6, be inserted into the abdominal cavity in the femoral veins 61 of the patient 62. In principle, the venous reservoir can also be employed without the implant 10 that has been described in preferred exemplary embodiments in FIGS. 1 through 5. Preferably, the venous reservoir is less elastic and less stretchable than the implant 10.

Figure 7:
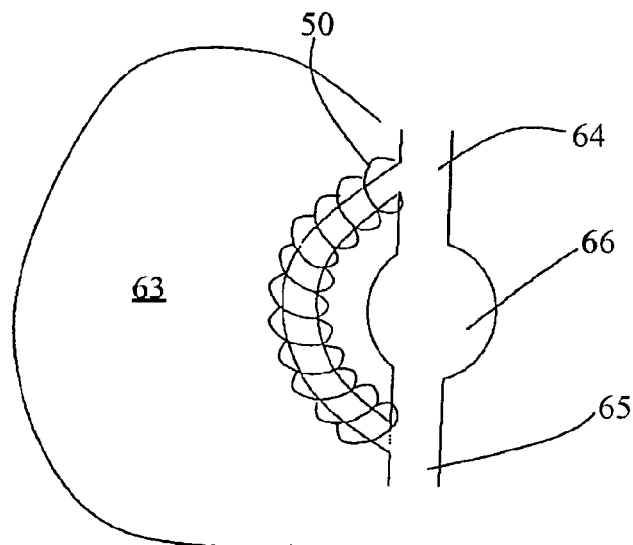
FIG. 7 shows a second exemplary embodiment for the venous reservoir.

FIG. 7 shows a further exemplary embodiment of the venous reservoir. The reservoir 50 of FIG. 7 is inserted into the lung cavity 63.

The helical or spiral reservoir 50 serves to hold blood volume in the venous system between the upper vena cava 64 and the lower vena cava 65, so that a certain blood volume in the right atrium 66 can be shifted or kept at a desired pressure level. The reservoir is wound around its own axis, so as to minimize its external dimensions and maximize its internal volume.

The invention claimed is:

1. A bypass device implant for lowering high blood pressure, comprising:
- a connector for connecting to a natural cardiovascular system;
- a volumetric chamber attached to the connector for receiving blood therein from the natural cardiovascular system, and a change in volume of the volumetric chamber is enabled or effected upon a pressure change in the cardiovascular system or in the volumetric chamber, wherein the change in volume in a lower pressure range between 50 mmHg and a pressure threshold value amounting to at least 120 mmHg amounts to at most 3 cm$^3$, and in an upper pressure range between the pressure threshold value and 150 mmHg amounts to at least 25 cm$^3$.

2. The bypass device of claim 1, wherein the volumetric chamber comprises a tube, and the connector comprises a ring at each end of the tube for connecting to the natural cardiovascular system, wherein blood from the natural cardiovascular system flows through the tube.

3. The bypass device of claim 1, wherein the pressure threshold value amounts to at least 130 mmHg.

4. The bypass device of claim 1, wherein the pressure threshold value amounts to at least 140 mmHg.

5. The bypass device of claim 1, wherein the pressure threshold value is adjustable.

6. The bypass device of claim 1, further comprising a controller including a sensor with which a pressure in the cardiovascular system or in the volumetric chamber is detectable.

7. The bypass device of claim 6, wherein the controller generates a signal when the pressure threshold value or a value correlating with the pressure threshold value is attained.

8. The bypass device of claim 1, further comprising an external guard against an ingrowth into and/or growth of natural tissue onto the volumetric chamber.

9. The bypass device of claim 1, wherein the implant device is adapted to be connected parallel to an upper portion of an aorta of the natural cardiovascular system.

* * * * *